United States Patent [19]
Mauck et al.

[11] Patent Number: 5,344,753
[45] Date of Patent: Sep. 6, 1994

[54] DRY ANALYTICAL ELEMENT AND METHOD FOR THE DETECTION OF AN AMINOPEPTIDASE OR TRANSPEPTIDASE

[75] Inventors: John C. Mauck, Rochester; Harold C. Warren, III, Rush; John W. Harder, Rochester, all of N.Y.

[73] Assignee: Eastman Kodak Company, Rochester, N.Y.

[21] Appl. No.: 891,150

[22] Filed: Jun. 1, 1992

[51] Int. Cl.⁵ .................... C12Q 1/00; C12Q 1/37; G01N 21/00
[52] U.S. Cl. ........................ 435/4; 435/16; 435/24; 435/25; 435/805; 422/56; 422/57; 436/169; 436/170
[58] Field of Search ............ 435/4, 16, 24, 25, 805; 422/56, 57; 436/169, 170

[56] References Cited

U.S. PATENT DOCUMENTS

| | | | |
|---|---|---|---|
| 4,390,343 | 6/1983 | Walter | 436/518 |
| 4,588,836 | 5/1986 | Matsumoto | 562/448 |
| 4,681,841 | 7/1987 | Matsumoto | 435/18 |
| 4,732,736 | 3/1988 | Robayashi | 422/56 |
| 4,776,904 | 10/1988 | Charlton | 156/73.1 |

FOREIGN PATENT DOCUMENTS

| | | |
|---|---|---|
| 58-170499 | 10/1983 | Japan . |
| 8175495A | 10/1983 | Japan . |
| 047697A | 3/1985 | Japan . |
| 0234837 | 2/1990 | Japan . |
| 0234838 | 2/1990 | Japan . |
| 0234839 | 2/1990 | Japan . |
| 0234840 | 2/1990 | Japan . |
| 0234841 | 2/1990 | Japan . |
| 0234843 | 2/1990 | Japan . |
| 0243540 | 2/1990 | Japan . |
| 02167545 | 6/1990 | Japan . |

*Primary Examiner*—Michael G. Wityshyn
*Assistant Examiner*—Ralph Gitomer
*Attorney, Agent, or Firm*—J. Lanny Tucker

[57] ABSTRACT

A dry analytical element has been prepared for the assay of leucine aminopeptidase at a pH of 6.5 to 11. The element zone contains an aromatic substrate for the enzyme. This substrate provides an aromatic reactant which has a primary amino group on the aromatic ring in the ortho or para position to an electron donor group. The aromatic reactant is oxidized with an oxidizing compound (such as an oxidase) and the oxidized compound reacts with a ballasted color-forming coupler to provide a dye.

19 Claims, 3 Drawing Sheets

DRY ANALYTICAL ELEMENT AND METHOD FOR THE DETECTION OF AN AMINOPEPTIDASE OR TRANSPEPTIDASE

FIELD OF THE INVENTION

The present invention relates to clinical chemistry. In particular, it relates to an analytical element and method for the determination of an aminopeptidase or transpeptidase in aqueous liquids, such as biological fluids.

BACKGROUND OF THE INVENTION

Peptidase is known as a general term for an enzyme which acts on a peptide bond in an L-peptide, splitting at the N-terminal to liberate amino acids or lower peptides. Such enzymes include, but are not limited to, leucine aminopeptidase, cysteine aminopeptidase, proline aminopeptidase, arginine aminopeptidase, alanine aminopeptidase and gamma-glutamyl transpeptidase.

Leucine aminopeptidase and gamma-glutamyl transpeptidase are widely distributed in human tissues and certain body fluids, such as serum. These enzymes increase in concentration in certain disease states, and are thus important clinical indicators for clinical diagnosis and treatment.

In particular, leucine aminopeptidase is an enzyme capable of liberating leucine from L-peptides, and particularly from those peptides having amino-terminal leucine groups. Its concentration has been known to vary greatly with certain health states. For example, it increases in the serum of people suffering from acute hepatitis, hepatoma, metastic hepatoma, liver cirrhosis or cholangia.

Gamma-glutamyl transpeptidase is clinically important in the diagnosis of cholestatic hepatitis, obstructive jaundice and primary metastatic hepatoma, active chronic hepatitis and non-active chronic hepatitis.

Known assays for leucine aminopeptidase or gamma-glutamyl transpeptidase activity generally involve the release of amine compounds from substrates by the enzyme to provide a colorimetric signal. Various substrates have been developed and described in the art for this very purpose, such as those described in U.S. Pat. No. 4,209,459 (Nagasawa et al), U.S. Pat. No. 4,588,836 (Matsumoto et al) and U.S. Pat. No. 4,681,841 (Matsumoto et al), and by Shimamoto et al, *Clin. Chem.*, 31, pp. 1636–1639, 1985. The assays described in these references and in many others not cited here are carried out in solution to yield a water-soluble dye if the enzyme is present in the serum specimen. Urine has also recently been tested to yield information about leucine aminopeptidase.

In recent years, analytes have been detected to great advantage using dry analytical elements which contain all of the appropriate reagents for the assay. In preferred dry elements, a topmost porous layer is used for spreading a specimen uniformly for contact with reagents in the element. Such spreading layers are prepared from a number of materials including a structure of adhered particles as described, for example, in U.S. Pat. No. 4,258,001 (Pierce et al) and pigmented layers such as those described in U.S. Pat. No. 3,992,158 (Przybylowicz et al). Pigmented layers containing titanium dioxide are often preferred for reduction of interferences, and ease of coating and finishing of the element.

It would be desirable to carry out the known assays for leucine aminopeptidase in a dry analytical element. However, there are a number of problems with doing so. Most of the dyes produced in known assays provide a signal at 400 nm or below which increases the risk of interference from bilirubin or hemoglobin. Moreover, some known substrates for the enzyme are toxic and require special handling and disposal.

In U.S. Pat. No. 4,681,841 (noted above), a useful dye is generated for detection at higher wavelength, but the color couplers used to generate the dye are water-soluble. This property presents additional problems for their use in dry analytical elements because the color couplers can migrate throughout the element, thereby reducing the observable dye signal. Moreover, the pH of the assay is critical for obtaining desired enzyme activity and sensitivity. Assay pH is easily controlled in solution assays, but it is difficult to control the pH when using dry analytical elements.

It would be highly desirable to be able to detect an aminopeptidase or transpeptidase in a dry analytical element whereby the reagents are kept separate and the pH is strictly controlled for optimum results. The known technology does not suggest how to solve these problems.

SUMMARY OF THE INVENTION

The problems noted above have been solved with an analytical element for the determination of an aminopeptidase or transpeptidase comprising, in fluid contact, a plurality of zones, a first zone being a porous spreading zone, and a second zone containing an oxidizing compound and a non-diffusible color-forming coupler, the element containing in a zone other than the second zone, an aromatic substrate which upon reaction with an aminopeptidase or transpeptidase provides a reactant having a primary amino group on a phenyl ring and a hydroxy, amino or substituted amino group in the ortho or para position to the primary amino group, and the element further containing in one or more of the zones, a buffer which is present in an amount effective to provide a pH of from about 6.5 to about 11 during an assay of a biological fluid for an aminopeptidase or transpeptidase, the non-diffusible color-forming coupler having the properties of:

a) being capable of undergoing electrophilic substitution, b) comprising a ballasting group which has a molecular weight of at least about 150, c) solubility in organic solvents having a molecular weight of at least about 150 and a boiling point of at least about 150° C., and d) when coupled with the oxidized form of the primary amino-containing reactant provided by the aromatic substrate, it will provide a dye having an absorbance in the range of from about 400 to about 800 nm, the oxidizing compound in the second zone being a compound which oxidizes the primary amino group of the primary amino-containing reactant to render it suitable for reaction with the color-forming coupler to form a dye.

This invention also provides a method for the determination of an aminopeptidase or transpeptidase comprising the steps of:

A. contacting a fluid sample suspected of containing an aminopeptidase or transpeptidase with the analytical element described above to form a dye, and
B. detecting the formation of the dye at an absorbance in the range of from about 400 to about 800 nm as an indication of the presence of the aminopeptidase or transpeptidase in the fluid sample.

This invention provides a simple, relatively rapid and sensitive means for assay of an aminopeptidase or transpeptidase, such as leucine aminopeptidase, gamma-glutamyl transpeptidase, cysteine aminopeptidase and others, which has all the known advantages of dry analytical systems. The dry element is readily adapted to automated assay equipment and is dry to the touch. In addition, the present invention effectively incorporates a color-forming coupler in the element which will not migrate and cause loss of dye signal. Moreover, the color-forming coupler is not toxic and provides high sensitivity. Use of a spreading layer advantageously reduces interferences arising from unwanted substances in biological specimens. Assay pH is carefully controlled in the element by use of a buffer in one or more of the zones so that sensitivity is optimized. Interference from hemoglobin or bilirubin is avoided.

These advantages are particularly achieved by use of certain color-forming couplers which are located in a zone of the element separate from that containing the aromatic substrate for the analyte. The color-forming coupler has the following properties:

a) it is capable of undergoing electrophilic substitution,
b) it comprises a ballasting group which has a molecular weight of at least about 150,
c) it is soluble in organic solvents having a molecular weight of at least about 150 and a boiling point of at least about 150° C., and
d) when coupled with the oxidized form of the primary amino-containing reactant provided by the aromatic substrate, it will provide a dye having an absorbance in the range of from about 400 to about 800 nm.

Because the coupler is ballasted, it cannot migrate into other layers. Yet, it is available for reaction with other reagents because they can readily move throughout the zones of the element.

DETAILED DESCRIPTION OF THE INVENTION

Figure 1:
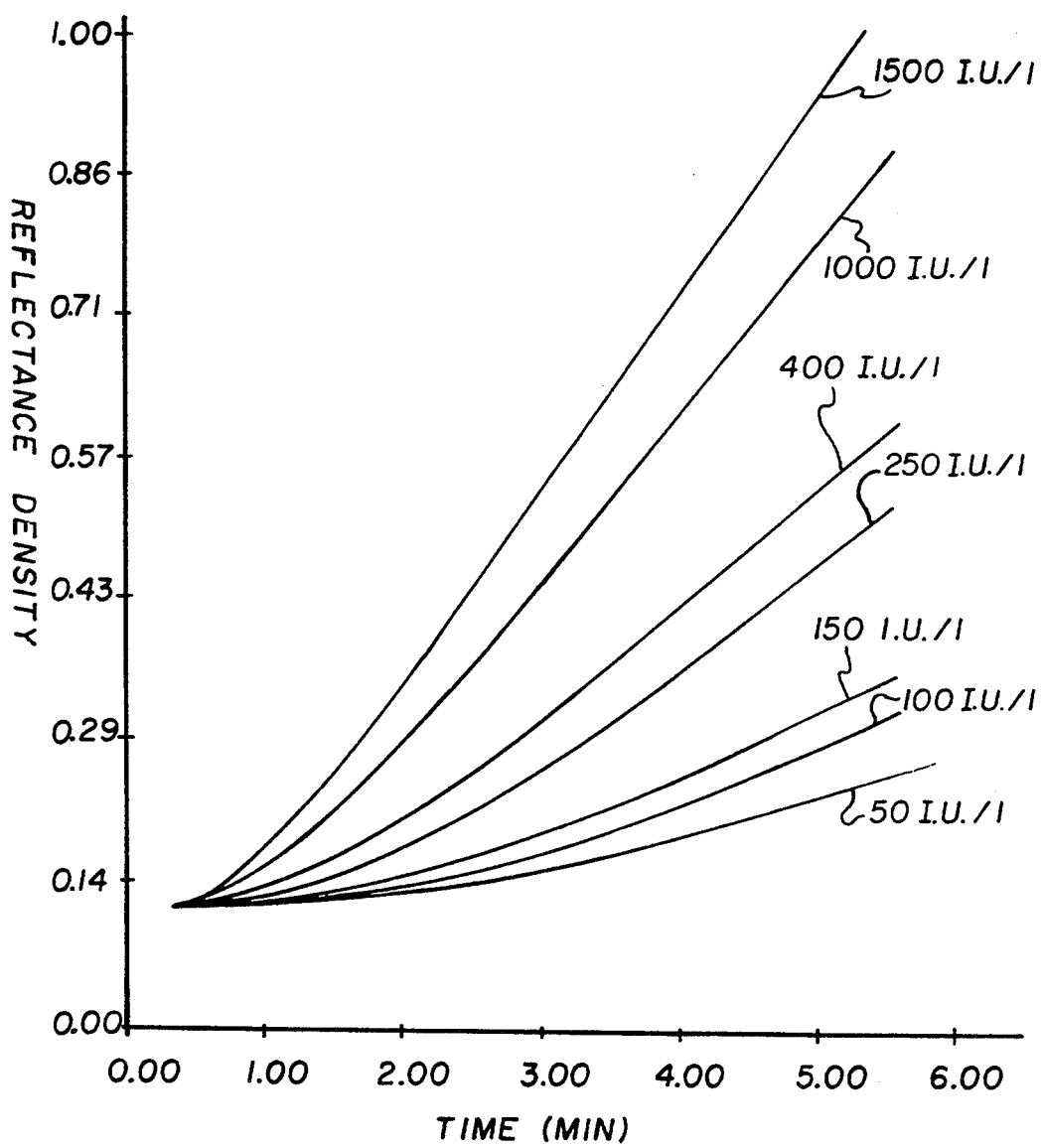
FIG. 1 is a graphical representation of reflectance density data generated over time for the determination of various concentrations (50–1500 I.U./liter) of leucine aminopeptidase using the element described in Example 1.

The present invention relates to a determination (either quantitative or qualitative) of an aminopeptidase or transpeptidase including, but not limited to, leucine aminopeptidase, gamma transpeptidase, cysteine aminopeptidase, proline aminopeptidase, arginine aminopeptidase and alanine aminopeptidase. In particular, the invention can be used to assay any aqueous fluid suspected of containing the enzyme, and particularly biological fluids including, but not limited to, sera, urine, lymph, plasma, whole blood and cerebral spinal fluid. It is also possible to assay fluid preparations of tissue such as preparations of liver or intestinal tissue. Preferably, human serum or urine is assayed with this invention.

The dry element of this invention has two or more contiguous zones (or layers) which are fluid permeable and contain all of the reagents needed for the detection of the enzyme analyte. The elements are known as test strips, test slides or diagnostic devices. The zones can be "self-supporting", which means that the zones can be composed of materials which maintain their integrity when exposed to aqueous fluids, such as filter papers or microporous membranes. Preferably, however, such zones are disposed on a separate, nonporous support which is dimensionally stable, inert to chemical reaction and preferably transparent (that is, radiation transmissive for wavelengths between about 200 and 900 nm). However, non-transparent supports can be used if the mode of detection is reflectance spectroscopy instead of transmission spectroscopy. Useful supports are well known in the art, including but not limited to polyesters, papers, metal foils and polystyrene, polycarbonates and cellulose esters.

At least one zone of the element (and preferably, the outermost zone), is a porous spreading zone prepared from any of the known materials used for such zones as described, for example in U.S. Pat. No. 4,292,272 (Kitajima et al), U.S. Pat. No. 3,992,158 (noted above), U.S. Pat. No. 4,258,001 (noted above) U.S. Pat. No. 4,430,436 (Koyama et al) and related U.S. patents, and JP 57(1982)-101760 (published Jun. 24, 1982). It is desired that the spreading zone be isotropically porous, meaning that the porosity is the same in each direction in the zone as caused by interconnected spaces or pores between particles, fibers or polymeric strands.

Preferred spreading zones are those described in U.S. Pat. No. 3,992,158 as "blush polymer" zones. Such zones can be formed on a supporting material by dissolving a polymer in a mixture of two organic liquids, one of which is a lower boiling, good solvent for the polymer and other being a high boiling, non-solvent or poor solvent for the polymer. The resulting polymer solution is coated on the supporting material and dried under controlled conditions to leave an isotropically porous zone. Various polymers are known to be useful in this context including, but not limited to, polycarbonates, polyamides, polyurethanes and cellulose esters such as cellulose acetate (which is preferred).

Within the porous zone can be incorporated particulate materials of various sizes to enhance the void volume. Useful particulate materials include, but are not limited to, inorganic pigments such as titanium dioxide, barium sulfate, zinc oxide, lead oxide with titanium dioxide being preferred. Further details of the preparation of "blush polymers" are described in U.S. Pat. No. 3,992,158.

The elements contain at least one other zone which contains one or more reagents needed for the assay. Such a zone is often known in the art as a reagent or registration zone, but it can also include a second porous spreading zone if desired or printed layers located on other zones. The zones are generally in fluid contact with each other, meaning that fluids, reagents and reagent products can pass or be transported between superposed regions of adjacent zones, unless of course, a reagent is immobilized in some manner so it will not migrate within or without a zone (see below with regard to color-forming couplers). Preferably, the zones are separately coated and superposed layers on an inert support (see Example 1 below). The reagent zones or layers can be composed of one or more binder materials (such as gelatin and other colloidal materials, hydrophilic polymers such as polyvinyl alcohol, polyacrylamide and others known in the art) in which reagents are incorporated.

The methods of preparing such elements are well known in the art and involve application of wet formulations of the zone composition onto a support and drying under suitable conditions. Coating procedures are well described in the art cited above for describing the spreading zones.

The assay of this invention is carried out with the following sequence of reactions, illustrated for leucine aminopeptidase:

a) leucine aminopeptidase catalyzes the conversion of an aromatic leucine aminopeptidase substrate into L-leucine and an aromatic reactant having a primary amino group which is ortho or para to a hydroxy, amino or substituted amino group on the ring, b) the one or more primary amino groups of the aromatic reactant are oxidized to one or more reactive imine groups with an oxidizing compound (the resulting oxidized compound can be a quinonimine or a quinondiimine), and c) the resulting imine (or diimine)-containing aromatic compound is reacted with a non-diffusible color-forming coupler to provide a dye.

A substrate for the enzyme analyte is provided in one of the zones of the element other than the zone which contains the color-forming coupler. In one embodiment, it can be included in the porous spreading zone described above. In another embodiment, it can be located in yet a different (or third) zone (or layer).

The substrate is aromatic and capable, upon reaction with the enzyme, of providing a reactant having a primary amino group on the aromatic ring (such as a phenyl ring), and also has a hydroxy, amino or substituted amino group in the ortho or para position to the primary amino group. Substitution in the para position is preferred. Substituted amino groups include, but are not limited to, methylamino, dimethylamino, isopropylamino and diethylamino.

In a preferred embodiment, the aromatic substrate is represented by the structure (I):

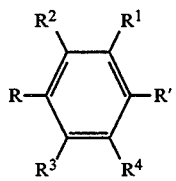

wherein R is an amino acid or peptide amido group which is the condensation product of a carboxylic acid group of an amino acid or peptide with a primary amino group appended to the aromatic ring. Examples of R include, but are not limited to, L-leucylamido, cysteinylamido, prolylamido, arginylamido, alanylamido, gamma-glutamylamido and others which would be apparent to one skilled in the art.

More preferably, R is $-NH-CO-R^5$ wherein $R^5$ is linear or branched alkyl having 1 to 6 carbon atoms (such as methyl, ethyl, isopropyl, t-butyl, pentyl and hexyl) which is substituted with at least one primary amino group. $R^5$ can also be substituted with one or more phenyl or substituted phenyl (such as hydroxyphenyl), p-aminophenyl, imidazolyl, indolyl, hydroxy, methylthio or other groups readily apparent to one skilled in the art. Representative $R^5$ groups include, but are not limited to 1-amino-3-methylbutyl, 1-amino-2-mercaptoethyl, 1-amino-4-guanidinobutyl, 1-aminoethyl, 1-aminophenethyl, 1-amino-3-carboxypropyl, 1-amino-2-carboxyethyl, 1-amino-2-(5-imidazolyl)ethyl, 1-amino-2-(4-hydroxyphenyl)ethyl, 1-amino-2-carbamoylethyl, 1-amino-2-carbamoylpropyl, 1-amino-2-hydroxyethyl, 1,5-diaminopentyl, 1-amino-2-hydroxypropyl, aminomethyl, 1-aminoethyl, 1-amino-2-methylpropyl, 1-amino-2-methylbutyl, 1-amino-3-methylbutyl, 1-amino-3-methylthiopropyl and 1-amino-2-(3-indolyl)ethyl. Most preferably, R is L-leucylamido (that is, $R^5$ is 1-amino-3-methylbutyl).

In structure (I) noted above, R' is hydroxy, or primary, secondary or tertiary amino (substituted with one or more lower alkyl groups of 1 to 6 carbon atoms, such as methyl, ethyl, isopropyl and t-butyl). Preferably, R' is hydroxy.

Also, each of $R^1$, $R^2$, $R^3$ and $R^4$ can independently be hydrogen, halo (for example fluoro, chloro or bromo), alkyl of 1 to 6 carbon atoms (such as methyl, ethyl, isopropyl, chloromethyl and methoxymethyl), alkoxy of 1 to 6 carbon atoms (such as methoxy, ethoxy, isopropoxy and t-butoxy), hydromy or amino (primary, secondary or tertiary). Preferably, $R^1$ and $R^4$ are independently halo (such as chloro or bromo) and each of $R^2$ and $R^4$ is hydrogen or methyl.

The substrates can optionally be used in the form of a salt, such as a formate, acetate, propionate, maleate, citrate, tartrate or oxalate. Examples of useful substrates are described in U.S. Pat. Nos. 4,209,459, 4,588,836, and 4,681,841.

A most preferred substrate is L-leucine-3,5-dibromo-4-hydroxyanilide useful for the determination of leucine aminopeptidase.

The aromatic substrates described above can be prepared using known procedures or purchased from various commercial sources, including Toyo Jozo (now part of Asahi Chemical Industry Co., Ltd.) of Japan. Preparatory procedures are described, for example, in U.S. Pat. Nos. 4,209,459 and 4,588,836.

In a second zone of the element is an oxidizing compound (or oxidant) which converts the primary amino-containing aromatic reactant to a compound having an imine group which can then react with the color-forming coupler (defined below). Useful oxidizing compounds include, but are not limited to, oxidases which consume oxygen when oxidizing the primary amino group. Other oxidizing compounds include ferric ethylenediaminetetraacetic acid (or equivalent salts) and cuprous chloride (or equivalent salts). Examples of useful oxidases include ascorbic acid oxidase, lactase, tyrosinase, aminophenol oxidase, phenol oxidase and polyphenol oxidase. Ascorbic acid oxidase, from any suitable source, is preferred as the oxidizing compound.

In the same zone as the oxidizing compound is a non-diffusible color-forming coupler which is used to provide a suitable dye in the element if the aminopeptidase or transpeptidase is present. The color-forming coupler must be capable of undergoing electrophilic substitution which means that the coupler has a "leaving" group (also known as an electrofuge) that is cleaved from the compound without its electron pair when displaced by an electrophile, that is a "positive attacking" group (a positive ion or positive end of a dipole or induced dipole). The "leaving" group can be, for example, hydrogen, mercapto, substituted mercapto (such as an organomercapto, for example methylthio, ethylthio, phenylthio, benzylthio and 2-pivalamidophenylthio), hydroxy, substituted or unsubstituted alkoxy of 1 to 12 carbon atoms (such as methoxy, ethoxy, isopropoxy, butoxy and octoxy), N-heterocyclic groups (such as pyrazolyl, imidazolyl and pyrrolyl) or halo (such as chloro and bromo). Preferably, the "leaving" group is hydrogen or substituted mercapto and 2-pivalaminophenylthio is most preferred. Electrophilic substitution is described in the art, for example, by March, *Advanced Organic Chemistry—Reaction Mechanisms and Structures*, 3rd Ed., John Wiley and Sons, New York, pages 447, 512 and 570.

The color-forming coupler comprises a ballasting group which has a molecular weight of at least about 150. That is, the ballasting group is of such size and configuration as to render the coupler non-diffusible. These groups can be substituted or unsubstituted with groups which enhance the non-diffusibility of the coupler, or modify the reactivity of the coupler. The ballasting group can contain a linking group through which it is joined to the coupler moiety. Such linking groups include, but are not limited to, oxy, thio, imino, carbonyloxy, sulfamoyl, sulfonamido, amido, carbamoyl and azo. Preferred ballasting groups include alkyl, aryl (substituted or unsubstituted), alkoxy, aryloxy, alkylthio and arylthio groups, each containing 8 to 32 carbon atoms as long as the molecular weight requirement is also met. Useful ballasting groups include, but are not limited to, dodecyl, tridecyl, tetradecanamido, 2-chloro-5-tetradecanamidoanilino, 4-(4-benzyloxyphenylsulfonyl)phenoxy, 3-tetradecylphenoxy, 4-butylsulfonamidophenoxy, 4-(2,5-di-t-pentylphenoxy)butylcarbamoyl, 2-ethyl-2-(3-tetradecylphenoxy)acetamido, 2-[4-(4-benzyloxyphenylsulfonyl)phenoxy]-2-decylacetamido, and substituted aryl such as trichlorophenyl. Other representative ballasting groups are described, for example, in U.S. Pat. No. 4,420,556 (Booms).

More preferably, the ballasting groups are alkyl (branched or linear), aryl or alkoxy (branched or linear) groups having 10 to 24 carbon atoms and substituted with one or more amino, amido, carbamoyl, sulfonamido or sulfamoyl groups. These groups can also be substituted with alkyl (1 to 25 carbon atoms), alkoxy (1 to 25 carbon atoms), halo, phenyl or phenyl substituted with alkyl (1 to 10 carbon atoms) or halo. Such preferred ballasting groups include alkyl, alkylamido, alkylamino, alkylcarbamoyl, alkylsulfonamido, alkylsulfamoyl, alkylamidoarylamino, aryloxy, aryloxyalkylamido, arylamino, arylamido, arylcarbamoyl, arylsulfonamido and arylsulfamoyl.

The color-forming coupler also has the property of being soluble in organic solvents, each having a molecular weight of at least about 150 and a boiling point of at least about 150° C. Examples of useful organic solvents include, but are not limited to, dibutyl phthalate, 2,4-di-n-pentylphenol, N,N-diethyllauramide, di-n-octyl phthalate, di-2-ethylhexyl phthalate and mixtures thereof.

Particularly useful color-forming couplers are those represented by the structures (II)–(V):

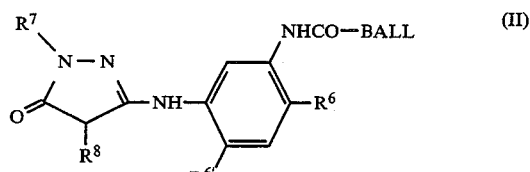  (II)

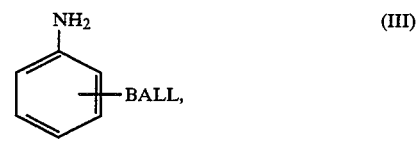  (III)

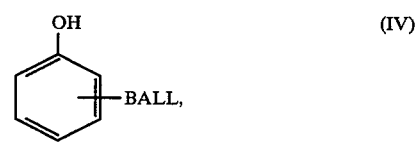  (IV)

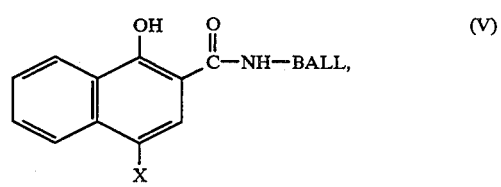  (V)

and

BALL—CO—CHR$^8$—CO—NHR$^{11}$  (VI)

(VI) BALL—CO—CHR$_8$—CO—NHR$^{11}$

In structure (II), $R^6$ and $R^{6'}$ are independently hydrogen, halo (for example, fluoro, chloro or bromo), —CONR$^9$R$^{10}$, —NR$^9$COR$^{10}$, —SO$_2$NR$^9$R$^{10}$, alkyl of 1 to 6 carbon atoms (such as methyl, isopropyl, hexyl and t-butyl) or alkoxy of 1 to 6 carbon atoms (such as methoxy, ethoxy, isopropoxy and hexoxy). Preferably, $R^6$ and $R^{6'}$ are independently hydrogen or halo and more preferably, $R^6$ is hydrogen and $R^{6'}$ is halo (such as chloro).

$R^7$ in structure (II) is phenyl or phenyl substituted with one or more halo (for example fluoro, chloro or bromo), alkyl of 1 to 5 carbon atoms (such as methyl, ethyl, isopropyl and chloromethyl) or alkoxy of 1 to 5 carbon atoms (such as methoxy, ethoxy and isopropoxy). Preferably, $R^7$ is trichlorophenyl.

Moreover, $R^8$ is hydrogen or a "leaving" group as defined above. Useful leaving groups are also defined above. Preferably, in structure II, $R^8$ is pivalamidophenylthio, and in structure VI, it is hydrogen.

$R^9$ is hydrogen, alkyl of 1 to 24 carbon atoms (such as methyl, ethyl, t-butyl, hexyl, dodecyl, pentadecyl and 3-methyloctyl), phenyl or phenyl substituted with one or more halo or alkyl groups as defined above for $R^7$. Preferably, $R^9$ is hydrogen.

$R^{10}$ is hydrogen or BALL wherein BALL is a ballast group as defined above.

$R^{11}$ is substituted or unsubstituted alkyl of 1 to 20 carbon atoms (such as methyl, ethyl, isopropyl, t-butyl, n-hexyl, octyl, nonyl, isononyl, decyl, dodecyl and hexadecyl), substituted or unsubstituted carbocyclic aryl of 6 to 14 carbon atoms in the ring (such as phenyl, naphthyl, anthryl, tolyl, xylyl, carbamoylphenyl, 3,5-dichlorophenyl and 4-cyanophenyl), heterocyclyl or BALL as defined above. Preferably, $R^{11}$ is aryl or heterocyclyl. When $R^{11}$ is heterocyclyl, it is a 5- or 6-membered ring of carbon atoms and at least one nitrogen, sulfur or oxygen atom, and optionally has one or two fused aromatic groups (such as benzo or naphtho) attached thereto. Any of the foregoing radicals defining $R^{11}$ can be substituted with one or more halo (such as fluoro, chloro, bromo or iodo), cyano, carboxy, substituted or unsubstituted alkyl as defined above, substituted or unsubstituted aryl as defined above, carbamoyl, sulfamoyl, alkylformamido or arylformamido (with alkyl and aryl defined as above), alkylsulfonamido or arylsulfonamido (with alkyl or aryl as defined above), alkoxy of 1 to 12 carbon atoms, aryloxy of 6 to 10 carbon atoms, alkoxycarbonyl (with alkoxy as defined above), aryloxycarbonyl (with aryloxy as defined above), acyl of 1 to 12 carbon atoms, acyloxy or 1 to 12 carbon atoms, or a BALL group as defined above.

In structure V, X is hydrogen, halo (such as chloro or bromo) or phenoxy (with or without substituents). Preferably, X is chloro or unsubstituted phenoxy.

In structure II, BALL is preferably alkyl or aryl as defined above.

The color-forming couplers having the structure (II) are preferred. Representative color-forming couplers are listed below with structure (VII) being most preferred.

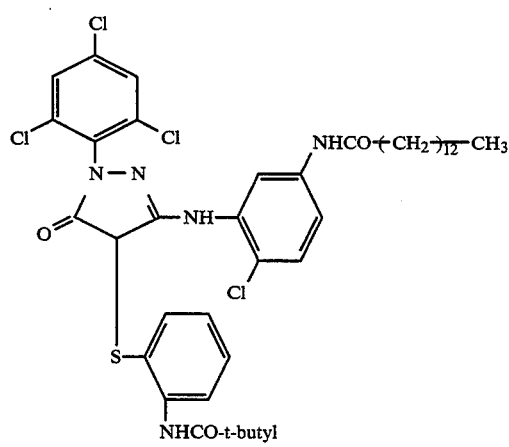
(VII)

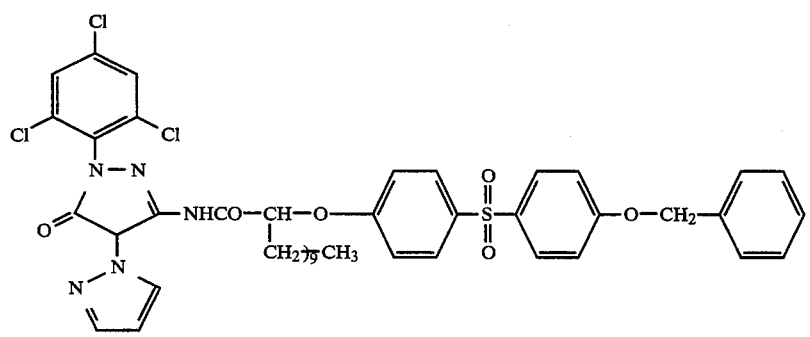
(VIII)

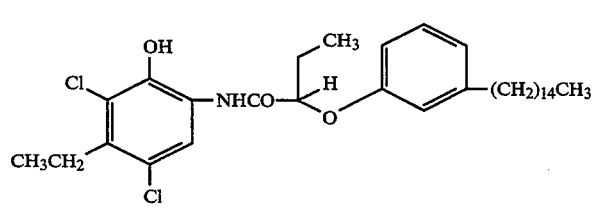
(IX)

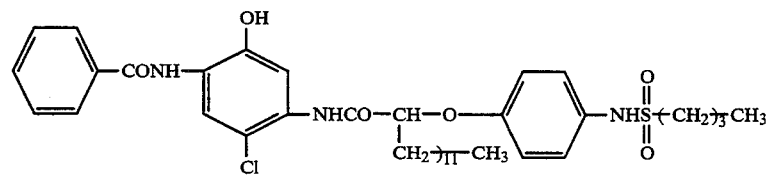
(X)

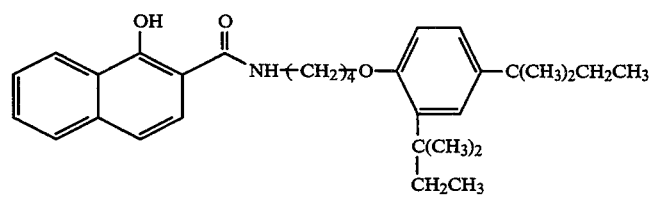
(XI)

The color-forming couplers as described herein can be prepared using conventional procedures and starting materials, as described for example, in U.S. Pat. No. 4,853,319 (Krishnamurthy). They are generally dissolved in organic solvents (described above) for coating purposes.

The elements of this invention can also contain one or more other addenda commonly included for various manufacturing or operational advantages. Such addenda include surfactants, ion chelating agents, buffers, organic solvents (such as organic solvents for the color-forming couplers), hardeners for binders, antioxidants, and others known in the art. Representative elements and components are described below in the examples. One or more buffers which maintain the pH within the element at from about 6.5 to about 11 during the assay are particularly useful. The assay is preferably carried out at a pH of from about 6.5 to about 9 with a pH of from about 8 to about 8.5 being most preferred. The buffer can be in any of the zones of the element. Acceptable buffers include, but are not limited to, tris(hydroxymethyl)aminomethane, glycine, borate and N-tris(hydroxymethyl)methyl-2-aminoethanesulfonic acid.

The amounts of reagents which can be incorporated within the element are generally within the skill of a worker in the art. More specifically, the aminopeptidase or transpeptidase aromatic substrate is present in a range of from about 0.05 to about 1 $g/m^2$, with an amount within the range of from about 0.2 to about 0.6 $g/m^2$ being preferred. The color-forming coupler is generally present in an amount of from about 0.05 to about 0.5 $g/m^2$, with from about 0.2 to about 0.4 $g/m^2$ being preferred. If the oxidizing compound is an oxidase, the generally useful amount is from about 1000 to about 50,000 I-U./$m^2$ with from about 10,000 to about 30,000 I-U./$m^2$ being preferred. Where the oxidizing compound is not an enzyme, the useful amount can be readily calculated to be that which would provide oxidizing capacity comparable to that of an oxidase. For example, for ethylenediaminepentaacetic acid (or salt), the amount on a molar basis would be from about 0.1 to about 2 molar/$m^2$.

As used in this application, one I.U. represents the International Unit for enzyme activity and is defined as the amount of enzyme activity required to catalyze the conversion of 1 micromole of substrate per minute under standard pH and temperature conditions. For the oxidases (for example ascorbic acid oxidase) described herein, the standard conditions are 37° C. and a pH of about 7.8.

The amounts of buffers and other addenda would be readily apparent to one skilled in the art given the teaching in the art and that provided in the examples below.

A variety of different elements, depending upon the method of assay, can be prepared in accordance with this invention. Elements can be configured in a variety of forms, including elongated tapes of any desired width, sheets, slides or chips.

In one embodiment of this invention, a multilayer element for the determination of an aminopeptidase comprises an inert polymeric support having thereon, in order and in fluid contact:

a first reagent layer containing the non-diffusible color-forming coupler and oxidizing compound as described above, a second reagent layer containing the aromatic substrate for the aminopeptidase as described above, and a porous spreading layer as described above, the element further comprising a buffer in one or more of the layers as described above.

In a preferred embodiment of this invention, a multilayer element comprises an inert polymeric support having thereon, in order and in fluid contact:

a reagent layer containing the non-diffusible color-forming coupler and oxidizing compound as described above, optionally a subbing layer (such materials being well known in the art), and a porous spreading layer as described above which contains the aromatic substrate for the enzyme analyte, the element further comprising a buffer in one or more layers as described above.

The assay of this invention can be manual or automated. In general, in using the dry elements, the enzyme analyte is determined by taking the element (for example from a supply roll, slide tray or packet) and physically contacting it on the porous spreading zone with a sample (for example from 1 to 200 µl) to be tested. The sample and reagents within the element then become mixed in the various zones. Such contact can be accomplished in any suitable manner, for example by dipping or immersing the element into the sample or preferably, by spotting the sample onto the element by hand or machine with a suitable dispensing means.

After sample application, the element is exposed to any conditioning, such as incubation, heating or otherwise, that may be desirable to quicken or otherwise facilitate obtaining a test result.

Generally within about 2 minutes, a first spectrophotometric measurement is made of any dye formed in the element. Since the analyte is an enzyme which reacts over time, generally a second measurement is taken a few minutes later. The rate of dye formation can be measured with suitable reflection or transmission spectrophotometric equipment and procedures as a measure of the enzyme activity.

The dye formed as a measure of the analyte is generally evaluated at a wavelength in the range of from about 400 to about 800 nm, with measurement at a wavelength of from about 500 to about 670 nm being preferred. In most cases, the wavelength measured is the maximum wavelength, although it is possible to evaluate many dyes off-peak (not at the maximum wavelength). The most preferred color-forming coupler identified as compound (VII) above provides a dye having a maximum wavelength at about 540 nm.

In the following examples which are used to illustrate, but not limit, the present invention, the materials used were commercially obtained as follows:

ESTANE ® polyurethane resin from B. F. Goodrich,

TRITON ® X-100, TRITON ® X-405 and TRITON ® X-705 surfactants from Rohm and Haas, BRIJ ® surfactant from ICI Americas, Inc.

tris(hydroxymethyl)aminomethane buffer from Sigma Chemical Co.,

L-leucine-3,5-dibromo-4-hydroxyanilide from Toyo Jozo, and the remainder of materials from either Eastman Kodak Company or other commercial sources, or they were prepared using standard procedures, or pro-

EXAMPLE 1

Multilayer Analytical Element for the Determination of Leucine Aminopeptidase

The element illustrated below was prepared by formulating the materials of each layer into coating dispersions using conventional procedures and solvents and coating them in the order shown using standard coating procedures.

| | | Layer Coverage (g/m²) |
|---|---|---|
| Spreading Layer | Titanium dioxide | 67 |
| | Cellulose acetate | 9.8 |
| | TRITON ™ X-405 | 1.85 |
| | BRIJ ™ 78 surfactant | 0.93 |
| | ESTANE ™ polyurethane resin | 1.8 |
| Subbing Layer | Poly(vinyl-pyrrolidone) | 0.94 |
| | or poly(N-iso-propylacryl-amide) | 0.39 |
| First Reagent Layer | Gelatin (unhardened) | 5 |
| | tris(hydroxy-methyl)amino-methane buffer | 1 |
| | TRITON ™ X-705 surfactant | 0.5 |
| | L-leucine-3,5-dibromo-4-hydroxyanilide | 0.3 |
| Second Reagent Layer | Gelatin (hardened) | 10 |
| | tris(hydroxy-methyl)amino-methane buffer | 3 |
| | TRITON ™ X-705 or TRITON ™ X-100 surfactant | 0.5 |
| | 2,4-di-n-pentylphenol | 2 |
| | Color-forming coupler (VII) | 0.2 |
| | Ascorbic acid oxidase | 25,000 I.U./m² |
| | Poly(ethylene-terephthalate) Support | |

The element was used to determine leucine aminopeptidase in the following manner.

Serum samples (10 μl each) containing various amounts (50–1500 I.U./liter) of leucine aminopeptidase were spotted on the porous spreading layer of individual elements. While the element was incubated at 37° C., reflectance density readings were recorded at 540 nm over a six minute time period. FIG. 1 shows the resulting dye signals over time for each sample, indicating that aminopeptidase can be acceptably determined using an element of this invention.

EXAMPLE 2

Preferred Analytical Element and Assay

This example demonstrates a preferred embodiment of this invention for the determination of leucine aminopeptidase whereby the aromatic substrate is located in the spreading layer.

The element of this example was like that shown in Example 1 except that the "First Reagent Layer" was eliminated. The substrate L-leucine-3,5-dibromo-4-hydroxyanilide (0.3 g/m²) was coated in the spreading layer. The assay was carried using the protocol described in Example 1.

Figure 2:
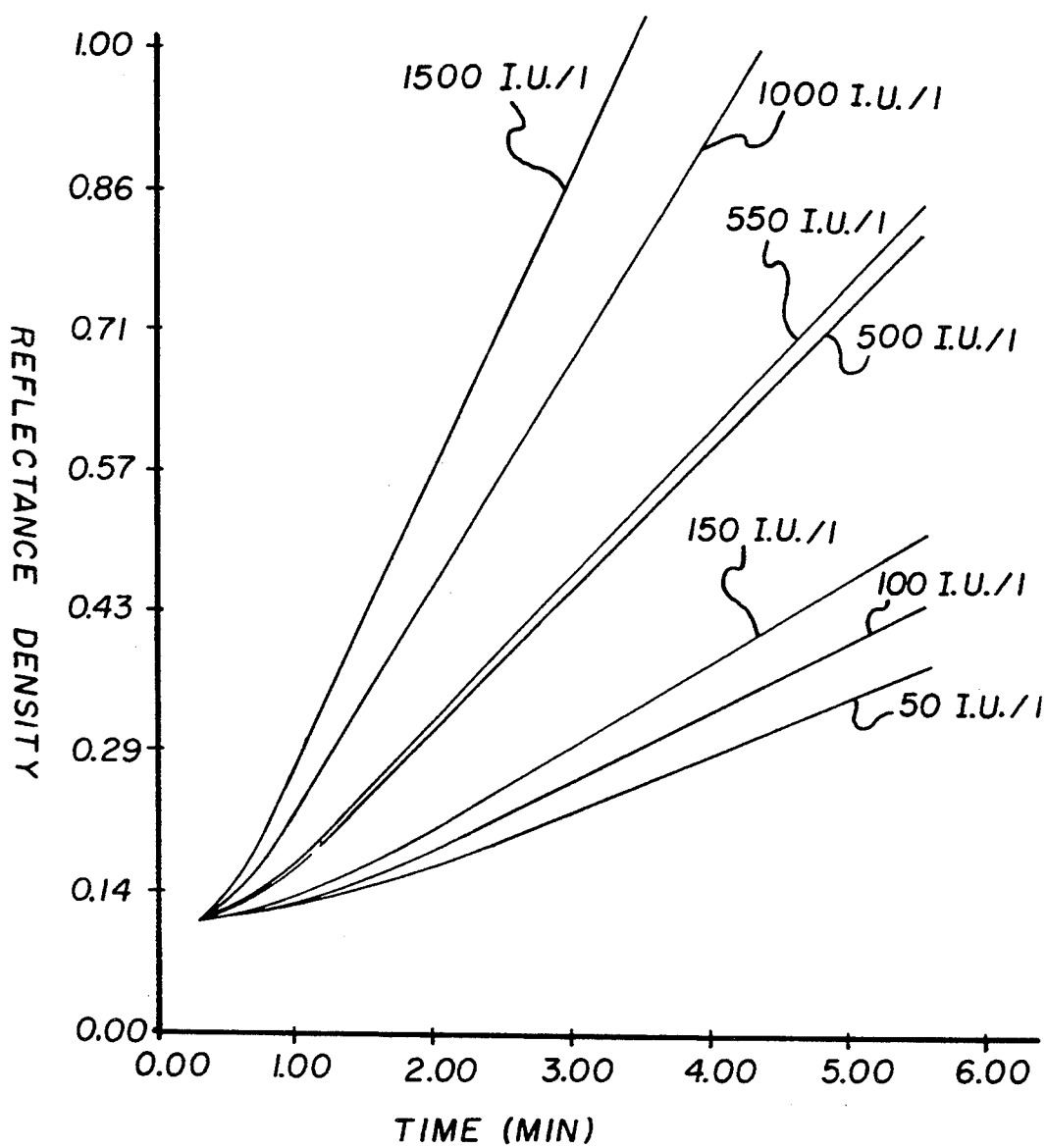
FIG. 2 is a graphical representation of reflectance density data generated over time for the determination of various concentrations (50–1500 I.U./liter) of leucine aminopeptidase using the element described in Example 2.

FIG. 2 shows the results of the dye signal (reflectance density) determinations (50–1500 I.U. analyte/liter) over the six minute time period. This embodiment is an improvement over that shown in Example 1 because the curves become linear more quickly (generally within two minutes). Thus, the assay can be performed in less time when the substrate is put into the spreading layer.

Figure 3:
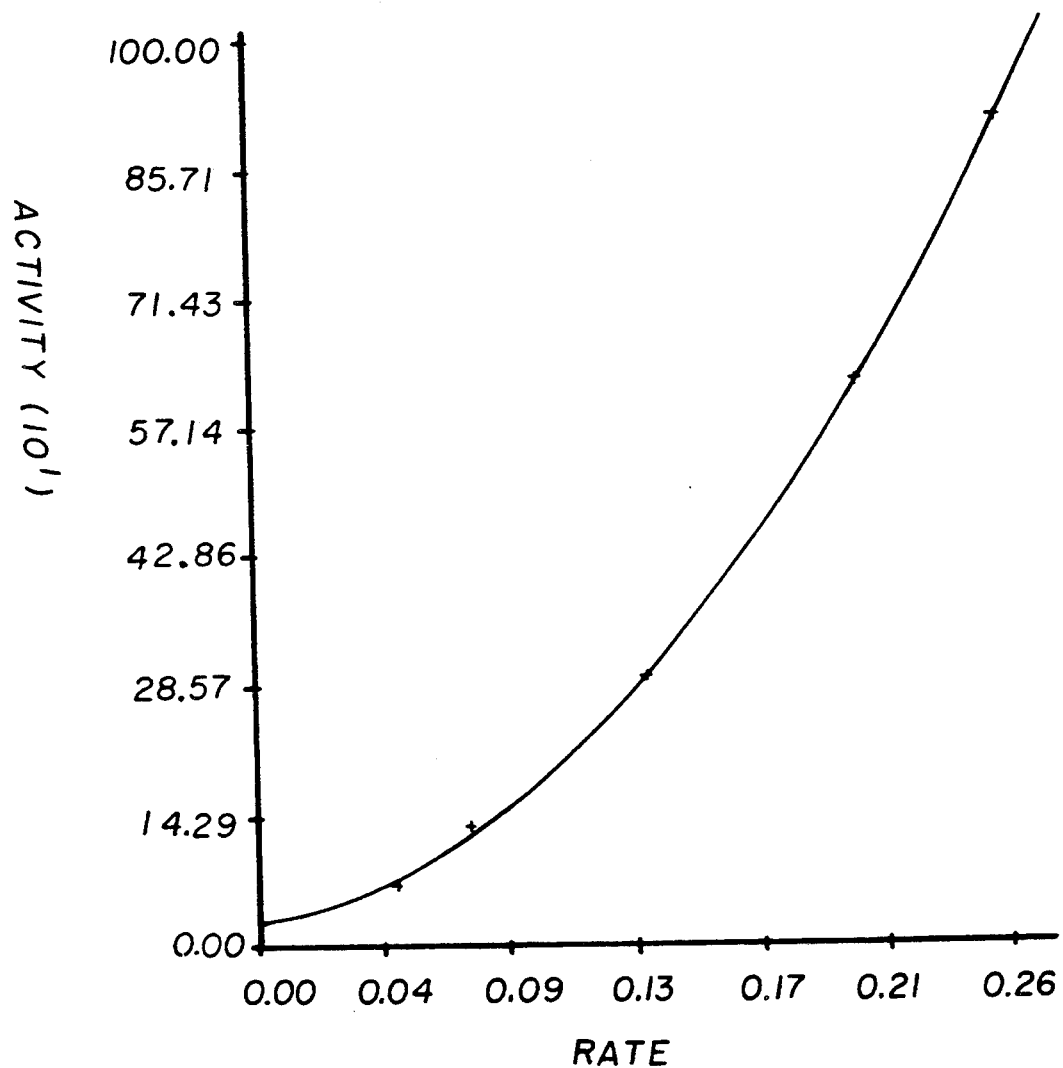
FIG. 3 is a calibration curve for the determination of leucine aminopeptidase using 50–1500 I.U./liter of enzyme analyte.

FIG. 3 is a calibration curve (activity vs. rate as measured by dye signal) generated using from 50 to 1500 I.U. analyte/liter.

The invention has been described in detail with particular reference to preferred embodiments thereof, but it will be understood that variations and modifications can be effected within the spirit and scope of the invention.

We claim:

1. An analytical element for the determination of an aminopeptidase or transpeptidase comprising, in fluid contact, a plurality of zones, a first zone being a porous spreading zone, and
    a second zone containing an oxidizing compound and a non-diffusible color-forming coupler,
    said element containing in a zone other than said second zone, an aromatic substrate which upon reaction with an aminopeptidase or transpeptidase provides a reactant having a primary amino group on a phenyl ring and a hydroxy, amino or substituted amino group in the ortho or para position to said primary amino group, and
    said element further containing in one or more of the zones, a buffer which is present in an amount effective to provide a pH of from about 6.5 to about 11 during an assay of a biological fluid for an aminopeptidase or transpeptidase,
    said non-diffusible color-forming coupler having the properties of:
    a) being capable of undergoing electrophilic substitution,
    b) comprising a ballasting group, BALL, which has a molecular weight of at least about 150,
    c) solubility in organic solvents having a molecular weight of at least about 150 and a boiling point of at least about 150° C., and
    d) when coupled with the oxidized form of said reactant provided by said aromatic substrate, said coupler will provide a dye having an absorbance in the range of from about 400 to about 800 nm,
    and said non-diffusible color-forming coupler having the structure:

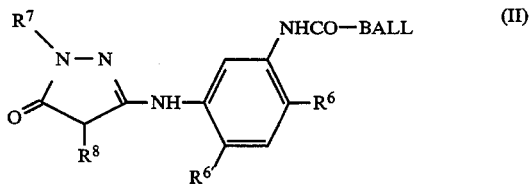

(II)

wherein $R^6$ and $R^{6'}$ are independently hydrogen, halo, —$CONR^9R^{10}$, —$NR^9COR^{10}$, —$SO_2NR^9R^{10}$, alkyl or alkoxy, $R^7$ is phenyl or phenyl substituted with halo, alkyl or alkoxy, $R^8$ is an organomercapto, $R^9$ is hydrogen, alkyl, phenyl or phenyl substituted with halo or alkyl, $R^{10}$ is hydrogen or BALL, and BALL is said ballasting group having 8 to 32 carbon atoms, said oxidizing compound in said second zone being a compound which oxidizes said primary amino group of said reactant to render the oxidized form of said reactant suitable for reaction with said color-forming coupler to form a dye.

2. The element of claim 1 wherein each of said zones are coated layers disposed on an inert polymeric support.

3. The element of claim 1 wherein said aromatic substrate is represented by the structure (I):

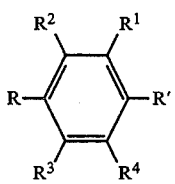

wherein R is an amino acid or peptide amido group which is the condensation product of a carboxylic acid group of an amino acid or peptide with a primary amino group appended to the aromatic ring, R' is hydroxy or amino, and $R^1$, $R^2$, $R^3$ and $R^4$ are independently hydrogen, halo, alkyl, alkoxy, hydroxy or amino.

4. The element of claim 3 wherein R is —NH—CO—$R^5$ wherein $R^5$ is alkyl which is substituted with at least one primary amino group, R' is hydroxy, $R^1$ and $R^4$ are independently halo, and each of $R^2$ and $R^3$ is hydrogen or methyl.

5. The element of claim 3 wherein said oxidizing compound is selected from the group consisting of an oxidase, ferric ethylenediaminetetraacetic acid and cuprous chloride.

6. The element of claim 1 wherein $R^7$ is trichlorophenyl, $R^8$ is 2-pivalamidophenylthio, and BALL is alkyl or aryl.

7. The element of claim 1 wherein $R^6$ and $R^{6'}$ are independently hydrogen or halo, $R^7$ is phenyl substituted with one or more halo, and $R^8$ is 2-pivalamidophenylthio.

8. The element of claim 1 wherein said buffer maintains the pH at from about 6.5 to about 9 during an assay of a biological fluid for an aminopeptidase or transpeptidase.

9. The element of claim 1 wherein said aromatic substrate is present in an amount of from about 0.05 to about 1 g/m², and said color-forming coupler is present in an amount of from about 0.05 to about 0.5 g/m².

10. A multilayer analytical element for the determination of leucine aminopeptidase comprising an inert polymeric support having thereon, in order and in fluid contact:

a first reagent layer containing an oxidizing compound and a non-diffusible color-forming coupler, a porous spreading layer containing an aromatic substrate which upon reaction with an aminopeptidase or transpeptidase provides a reactant having a primary amino group on a phenyl ring and a hydroxy, amino or substituted amino group in the ortho or para position to said primary amino group, said element further comprising in one or more of said layers, a buffer which is present in an amount effective to provide a pH of from about 6.5 to about 11 during an assay of a biological fluid for an aminopeptidase or transpeptidase.

said non-diffusible color-forming coupler having the properties of:

a) being capable of undergoing electrophilic substitution, b) comprising a ballasting group, BALL, which has a molecular weight of at least about 150, c) solubility in organic solvents having a molecular weight of at least about 150 and a boiling point of at least about 150° C., and d) when coupled with the oxidized form of said reactant provided by said aromatic substrate, said coupler will provide a dye having an absorbance in the range of from about 400 to about 800 nm, and said non-diffusible color-forming coupler having the structure:

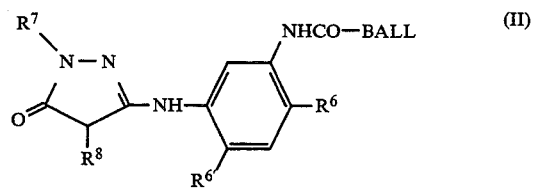

wherein $R^6$ and $R^{6'}$ are independently hydrogen, halo, —$CONR^9R^{10}$, —$NR^9COR^{10}$, —$SO_2NR^9R^{10}$, alkyl or alkoxy, $R^7$ is phenyl or phenyl substituted with halo, alkyl or alkoxy, $R^8$ is an organomercapto, $R^9$ is hydrogen, alkyl, phenyl or phenyl substituted with halo or alkyl, $R^{10}$ is hydrogen or BALL, BALL is said ballasting group having 8 to 32 carbon atoms, and said oxidizing compound in said first reagent layer being a compound which oxidizes the primary amine group of said reactant to render the oxidized form of said reactant suitable for reaction with said color-forming coupler to form a dye.

11. The element of claim 10 wherein said aromatic substrate is represented by the structure (I):

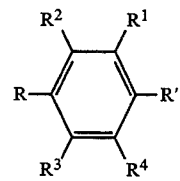

wherein R is an amino acid or peptide amido group which is the condensation product of a carboxylic acid group of an amino acid or peptide with a primary amino group, R' is hydroxy or amino, and $R^1$, $R^2$, $R^3$ and $R^4$ are independently hydrogen, halo, alkyl, alkoxy, hydroxy or amino, and said oxidizing compound is selected from the group consisting of an oxidase, ferric ethylenediaminetetraacetic acid and cuprous chloride.

12. A method for the determination of an aminopeptidase or transpeptidase comprising the steps of:

A. contacting a fluid sample suspected of containing an aminopeptidase or transpeptidase with an analytical element for the determination of an aminopeptidase or transpeptidase comprising, in fluid contact, a plurality of zones, a first zone being a porous spreading zone, and a second zone containing an oxidizing compound and a non-diffusible color-forming coupler, said element containing in a zone other than said second zone, an aromatic substrate which upon reaction with an aminopeptidase or transpeptidase provides a reactant having a primary amino group on a phenyl ring and a hydroxy, amino or substituted amino group in the ortho or para position to said primary amino group, and said element further containing in one or more of the zones, a buffer which is present in an amount effective to provide a pH of from about 6.5 to about 11 during an assay of a biological fluid for an aminopeptidase or transpeptidase, said non-diffusible color-forming coupler having the properties of:

a) being capable of undergoing electrophilic substitution, b) comprising a ballasting group, BALL, which has a molecular weight of at least about 150, c) solubility in organic solvents having a molecular weight of at least about 150 and a boiling point of at least about 150° C., and d) when coupled with the oxidized form of said reactant provided by said aromatic substrate, said coupler will provide a dye having an absorbance in the range of from about 400 to about 800 nm, said non-diffusible color-forming coupler having the structure:

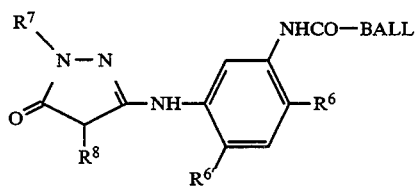

(II)

wherein $R^6$ and $R^{6'}$ are independently hydrogen, halo, —$CONR^9R^{10}$, —$NR^9COR^{10}$, —$SO_2NR^9R^{10}$, alkyl or alkoxy, $R^7$ is phenyl or phenyl substituted with halo, alkyl or alkoxy, $R^8$ is an organomercapto, $R^9$ is hydrogen, alkyl, phenyl or phenyl substituted with halo or alkyl, $R^{10}$ is hydrogen or BALL, and BALL is said ballasting group having 8 to 32 carbon atoms, and said oxidizing compound in said second zone being a compound which oxidizes said primary amino group of said reactant to render the oxidized form of said reactant suitable for reaction with said color-forming coupler to form a dye, and B. detecting the formation of said dye at an absorbance in the range of from about 400 to about 800 nm as an indication of the presence of the aminopeptidase or transpeptidase in said fluid sample.

13. The method of claim 12 wherein said dye is detected at a wavelength of from about 500 to about 670 nm.

14. The method of claim 12 wherein the reactions in said method are carried out at a pH of from about 6.5 to about 9.

15. The method of claim 12 wherein said fluid sample is human serum.

16. The method of claim 12 wherein said aromatic substrate is represented by the structure (I):

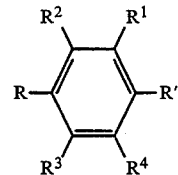

wherein R is an amine acid or peptide amido group which is the condensation product of a carboxylic acid group of an amine acid or peptide with a primary amine group appended to the aromatic ring, R' is hydroxy or amine, and $R^1$, $R^2$, $R^3$ and $R^4$ are independently hydrogen, halo, alkyl, alkoxy, hydroxy or amino, and said oxidizing compound is selected from the group consisting of an oxidase, ferric ethylenediaminetetraacetic acid and cuprous chloride.

17. The method of claim 16 for the determination of leucine aminopeptidase wherein said aromatic substrate is L-leucine-3,5-dibromo-4-hydroxyanilide, said oxidizing compound is ascorbic acid oxidase and said color-forming coupler has the structure:

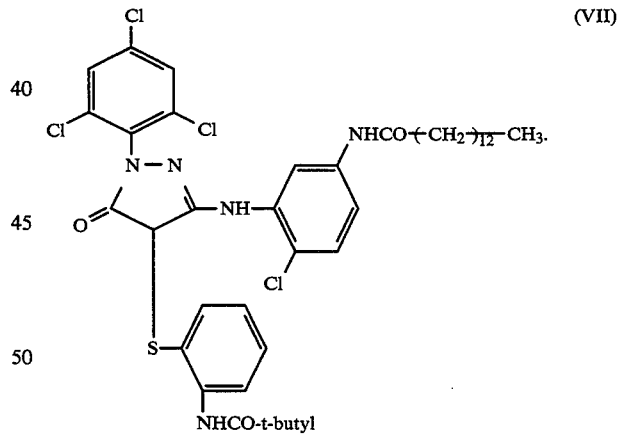

(VII)

18. The method of claim 12 wherein said element is a multilayer analytical element further comprising an inert polymeric support having thereon, in order and in fluid contact:

said second zone as a reagent layer, and said first zone as a porous spreading layer.

19. The method of claim 16 wherein R is —NH—CO—$R^5$ wherein $R^5$ is alkyl which is substituted with at least one primary amino group, R' is hydroxy, $R^1$ and $R^4$ are independently halo, and each of $R^2$ and $R^3$ is hydrogen or methyl, said color coupler has structure (II) wherein $R^7$ is trichlorophenyl, $R^8$ is 2-pivalamidophenylthio, and BALL is alkyl, aryl, alkoxy, aryloxy, alkylthio or arylthio.

* * * * *

UNITED STATES PATENT AND TRADEMARK OFFICE
CERTIFICATE OF CORRECTION

PATENT NO. : 5,344,753
DATED : September 6, 1994
INVENTOR(S) : Mauck, et. al.

It is certified that error appears in the above-indentified patent and that said Letters Patent is hereby corrected as shown below:

Column 6, line 35, delete "$R^4$" and insert in its place --$R^3$--.

Signed and Sealed this

Eleventh Day of February, 1997

Attest:

BRUCE LEHMAN

Attesting Officer

Commissioner of Patents and Trademarks